(12) United States Patent
Kozak et al.

(10) Patent No.: US 10,905,489 B2
(45) Date of Patent: Feb. 2, 2021

(54) MEDICAL DEFORMATION DEVICE, DEFORMATION SYSTEM AND METHOD FOR DEFORMING AN ARTICLE

(71) Applicant: Aesculap AG, Tuttlingen (DE)

(72) Inventors: Josef Kozak, Tuttlingen (DE); Jens Beger, Tuttlingen (DE); Dieter Weisshaupt, Immendingen (DE)

(73) Assignee: Aesculap AG, Tuttlingen (DE)

( * ) Notice: Subject to any disclaimer, the term of this patent is extended or adjusted under 35 U.S.C. 154(b) by 19 days.

(21) Appl. No.: 16/136,782

(22) Filed: Sep. 20, 2018

(65) Prior Publication Data

US 2019/0133665 A1 May 9, 2019

(30) Foreign Application Priority Data

Sep. 25, 2017 (DE) .......................... 10 2017 122 143

(51) Int. Cl.
| | |
|---|---|
| *A61B 17/88* | (2006.01) |
| *A61B 34/20* | (2016.01) |
| *A61B 17/70* | (2006.01) |
| *A61B 90/00* | (2016.01) |

(52) U.S. Cl.
CPC ...... *A61B 17/8863* (2013.01); *A61B 17/7013* (2013.01); *A61B 34/20* (2016.02); *A61B 2034/2055* (2016.02); *A61B 2034/2072* (2016.02); *A61B 2090/0811* (2016.02)

(58) Field of Classification Search
CPC ...... A61B 17/80; A61B 17/88; A61B 17/8863
See application file for complete search history.

(56) References Cited

U.S. PATENT DOCUMENTS

| | | | |
|---|---|---|---|
| 6,036,691 | A | 3/2000 | Richardson |
| 6,226,548 | B1 | 5/2001 | Foley et al. |
| 7,561,733 | B2 | 7/2009 | Vilsmeier et al. |
| 7,763,030 | B2 | 7/2010 | Blau et al. |
| 7,809,184 | B2 | 10/2010 | Neubauer et al. |
| 7,835,778 | B2 | 11/2010 | Foley et al. |
| 7,862,568 | B2 | 1/2011 | Vilsmeier et al. |
| 7,922,731 | B2 | 4/2011 | Schumacher et al. |

(Continued)

FOREIGN PATENT DOCUMENTS

| | | |
|---|---|---|
| DE | 10045375 | 4/2002 |
| DE | 10314882 | 10/2004 |

(Continued)

*Primary Examiner* — Julianna N Harvey

(74) *Attorney, Agent, or Firm* — Lipsitz & McAllister, LLC

(57) ABSTRACT

The invention relates to a medical deformation device for a medical article, said deformation device comprising a receptacle for fixing the article, a deformation tool used to act on the article for deformation purposes, the deformation tool being movable in a defined manner relative to the receptacle, and a medical marking device that is detectable by a navigation system is held in each case on the receptacle and on the deformation tool for the purposes of determining a relative position of the deformation tool and the receptacle, wherein a further marking device is fixed to the deformation tool for the purposes of determining, by means of the navigation system, an extent of a deformation of the article. Moreover, the invention relates to a deformation system and a method for deforming a medical article.

19 Claims, 3 Drawing Sheets

(56) References Cited

U.S. PATENT DOCUMENTS

| | | |
|---|---|---|
| 7,957,831 B2 | 6/2011 | Isaacs |
| 8,320,612 B2 | 11/2012 | Knobel et al. |
| 8,534,848 B2 | 9/2013 | Hauri et al. |
| 8,549,888 B2 | 10/2013 | Isaacs |
| 9,314,281 B2 | 4/2016 | Beger et al. |
| 9,414,859 B2 | 8/2016 | Ballard et al. |
| 9,585,700 B2 | 3/2017 | Wehrle et al. |
| 2003/0078565 A1 | 4/2003 | Vilsmeier et al. |
| 2005/0262911 A1 | 12/2005 | Dankowicz et al. |
| 2007/0160439 A1 | 7/2007 | Vilsmeier et al. |
| 2009/0249851 A1 | 10/2009 | Isaacs |
| 2011/0265538 A1* | 11/2011 | Trieu ............ A61B 17/8863 72/295 |
| 2011/0270262 A1* | 11/2011 | Justis ............ A61B 17/8863 606/101 |
| 2011/0286098 A1 | 11/2011 | Hauri et al. |
| 2013/0066387 A1 | 3/2013 | Beger et al. |
| 2013/0268007 A1 | 10/2013 | Rezach et al. |
| 2014/0225999 A1 | 8/2014 | Bracke et al. |
| 2014/0311203 A1 | 10/2014 | Crawford et al. |
| 2014/0316420 A1 | 10/2014 | Ballard et al. |
| 2015/0305786 A1 | 10/2015 | Wehrle et al. |
| 2016/0175013 A1 | 6/2016 | Redmond |
| 2016/0242857 A1 | 8/2016 | Scholl |
| 2017/0000568 A1 | 1/2017 | O'Neil et al. |
| 2017/0340367 A1 | 11/2017 | Beger et al. |

FOREIGN PATENT DOCUMENTS

| | | |
|---|---|---|
| DE | 102004008870 | 10/2004 |
| DE | 102005026654 | 12/2006 |
| DE | 102008022254 | 11/2009 |
| DE | 102010016448 | 10/2011 |
| DE | 202015100313 | 3/2015 |
| DE | 102014102398 | 8/2015 |
| DE | 102015102776 | 9/2016 |
| EP | 1281365 | 2/2003 |
| EP | 1413257 | 2/2005 |
| EP | 1657678 | 5/2006 |
| EP | 1719472 | 11/2006 |
| EP | 1523950 | 2/2009 |
| EP | 2910206 | 8/2015 |
| WO | 0159708 | 8/2001 |
| WO | 03020146 | 3/2003 |
| WO | 2009135838 | 11/2009 |
| WO | 2011020505 | 2/2011 |
| WO | 2013164770 | 11/2013 |
| WO | 2014088801 | 6/2014 |
| WO | 2016134911 | 9/2016 |
| WO | 2017037113 | 3/2017 |

* cited by examiner

MEDICAL DEFORMATION DEVICE, DEFORMATION SYSTEM AND METHOD FOR DEFORMING AN ARTICLE

CROSS-REFERENCE TO RELATED APPLICATIONS

This application claims the benefit of German application number 10 2017 122 143.3, filed on Sep. 25, 2017, which is incorporated herein by reference in its entirety and for all purposes.

FIELD OF THE INVENTION

The present invention relates to a medical deformation device for a medical article. Moreover, the present invention relates to a medical deformation system and a method for deforming a medical article.

BACKGROUND OF THE INVENTION

Medical fixation systems for fixing body structures relative to one another are known, wherein anchoring elements fixed to the body structures are connected to one another by means of a stabilization element. An exemplary field of application lies in the stabilization of vertebral bodies relative to one another, wherein bone screws are used as anchoring elements and a rod is used as a stabilization element. Such fixation systems are described in EP 2 910 206 A1 and WO 2016/134911 A1, for example. It is known practice here to establish the position of the anchoring elements which are fixed to the structures—i.e., bone screws that are fixed to the vertebral bodies, for example—relative to one another by means of a medical navigation system. With the proviso that the anchoring elements should be fixed to one another with a defined relative position, the shape of the stabilization element can be determined by the navigation system. Here, it is possible to establish a spatial curve, for example. On the basis of this information, it is possible to select a stabilization element from a store. As an alternative or in addition thereto, there is the option of converting the stabilization element into the shape of the spatial curve. To this end, the use of medical deformation devices is known, for example from WO 2016/134911 A1. The deformation device described therein has proven its worth in practice.

The present invention relates to a medical deformation device for a medical article, which is not restricted to a stabilization element and, in particular, a rod of a medical fixation system.

An object underlying the present invention is to provide a deformation device, a deformation system and a method of the type set forth at the outset, by means of which the deformation of a medical article is facilitated.

SUMMARY OF THE INVENTION

In a first aspect of the invention, a medical deformation device for a medical article comprises a receptacle for fixing the article, a deformation tool used to act on the article for deformation purposes, the deformation tool being movable in a defined manner relative to the receptacle, and a respective medical marking device that is detectable by a navigation system being held on the receptacle and on the deformation tool for the purposes of determining a relative position of the deformation tool and the receptacle. A further marking device is fixed to the deformation tool for the purposes of determining an extent of a deformation of the article by means of the navigation system.

In a second aspect of the invention, a medical deformation system comprises a deformation device in accordance with the first aspect and a medical navigation system for detecting and tracking the marking devices of the deformation device. The relative position of the receptacle and of the deformation tool is determinable by the navigation system for the purposes of determining a deformation position of the article. The extent of the deformation of the article at the deformation position is determinable with the navigation system.

In a third aspect of the invention, a method is provided for deforming a medical article. In the method, a deformation system in accordance with the second aspect is used to determine a deformation position of the medical article to be deformed and an extent of the deformation of the article at the deformation position is determined.

BRIEF DESCRIPTION OF THE DRAWINGS

The foregoing summary and the following description of preferred embodiments may be better understood in conjunction with the drawing figures. The deformation system described below allows the implementation of a preferred exemplary embodiment of a method according to the invention. In the drawings.

DETAILED DESCRIPTION

Figure 1:
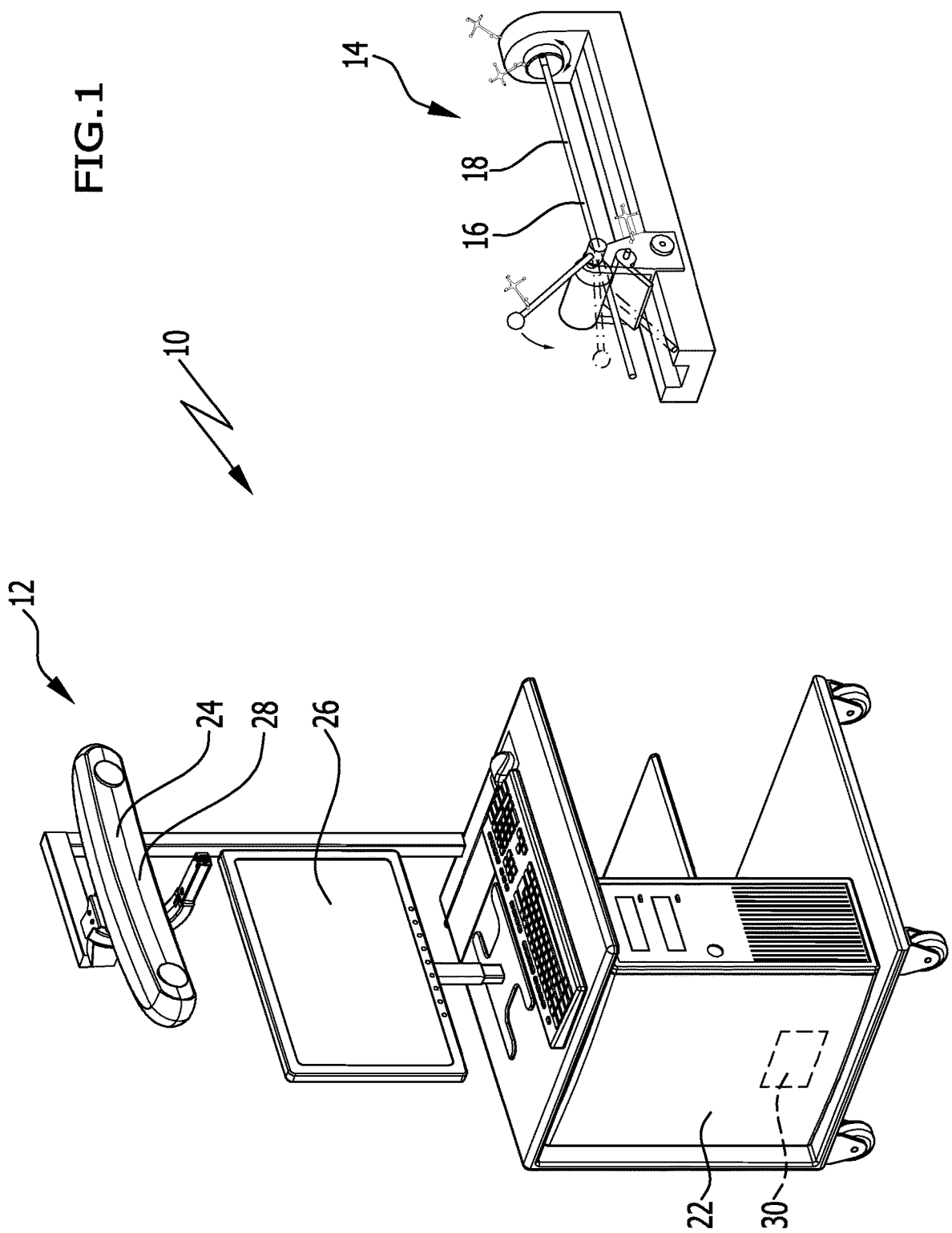
FIG. 1 shows a perspective schematic illustration of a deformation system according to the invention, comprising a navigation system and a preferred embodiment of a deformation device according to the invention.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical deformation device for a medical article. The medical deformation device comprises a receptacle for fixing the article, a deformation tool used to act on the article for deformation purposes, the deformation tool being movable in a defined manner relative to the receptacle, and a respective medical marking device that is detectable by a navigation system being held on the receptacle and on the deformation tool for the purposes of determining a relative position of the deformation tool and the receptacle. A further marking device is fixed to the deformation tool for the purposes of determining an extent of a deformation of the article by means of the navigation system.

The present invention is based on the consideration that, in order to provide the medical article with a desired shape, the position and the extent of the deformation can be checked comparatively easily using a medical navigation system. The article can be fixed to the receptacle and the deformation tool is used for deformation purposes. The relative position of the receptacle and of the deformation tool can be determined by means of a navigation system by virtue of, for example, the position and/or orientation of the marking devices held thereon being able to be determined by the navigation system, as a result of which the positions of the receptacle and of the deformation tool can be derived. To this end, the marking devices are configured differently and distinguishably from one another in the present case. This provides the option of positioning the deformation tool at a desired deformation position on the article, at which the deformation is undertaken. Additionally, a further marking device, which is distinguishable from the existing marking devices mentioned, is provided in order to determine the extent of the deformation of the article. The further marking device is held on the deformation tool and allows the navigation system, for example, to determine whether the deformation at the desired deformation position coincides with a desired deformation.

In particular, the deformation device according to the invention can have a purely mechanical configuration and can be easily operable in this way.

Advantageously, it is possible to undertake the deformation of the article without a priori knowledge about the desired deformation position and desired deformation. If a correct desired deformation position and desired deformation are adopted, a corresponding notification can be output to a user by means of the navigation system—this will be discussed in more detail below—and so the user can easily guide the deformation without, for example, entering deformation data into the deformation device.

By way of example, the deformation tool can be configured to be displaceable relative to the receptacle. Here, provision can be made of, in particular, a straight-lined displacement, for example along, or parallel to, an axis defined by the receptacle.

It is expedient if the deformation device comprises a holding device, which comprises or forms the receptacle or on which the receptacle is fixed, and that the deformation tool is held in movable manner on the holding device, wherein, preferably, provision can be made of a securable, movable holding of the deformation tool on the holding device. The receptacle is arranged on the holding device and the deformation tool can be moved relative to the receptacle when held on the holding device. This simplifies the handling of the deformation device for an operator.

Advantageously, the holding device comprises or forms a guide for a bearing body of the deformation tool. By way of the guide, bringing the deformation tool and the receptacle into a defined relative position is made easier for the user. A marking device of the deformation device is advantageously held on the bearing body.

It is advantageous if the deformation device comprises a medical marking device held on the holding device for the purposes of determining the position and/or orientation of the deformation device relative to the navigation system. The marking device which, in particular, differs from the marking devices specified above allows the navigation system to detect and, in particular, track the deformation device in terms of position and/or orientation. This makes it easier for the navigation system to check the desired deformation position and the desired deformation on the basis of the further marking devices.

Advantageously, provision is made for the receptacle is configured to be rotatable relative to the holding device, wherein the receptacle is preferably rotatably mounted on the holding device. Here, it is expedient if the receptacle defines an axis that is aligned with an axis defined by the article, said article having a longitudinal extent and being fixed in the receptacle. The deformation of the article is simplified by means of the rotatable receptacle relative to the holding device because a user is spared the need for, where necessary, removing the article from the receptacle and re-fixing the latter with a different orientation or position in the receptacle. Instead, only the receptacle can be rotated, particularly in the case of a rod-shaped article with longitudinal extent. The degree of freedom provided by the rotation can be monitored by the navigation system by means of the marking device held on the receptacle. This provides not only the option of checking the desired deformation position relative to the relative spacing of the deformation tool and the receptacle but also of checking the latter relative to the relative orientation of the article and the deformation tool, in dependence on a rotation.

There is conceivable a rotation of the receptacle relative to the holding device, said rotation being actuated manually or by means of a drive. The deformation device can comprise a corresponding drive.

Correspondingly, there is conceivable a movement and, in particular, a displacement of the deformation tool relative to the receptacle, said movement and, in particular, said displacement being actuated manually or by means of a drive. The deformation device can comprise a corresponding drive.

In an advantageous embodiment, provision can be made for the deformation tool to be a bending tool and to comprise a bending body and, coupled therewith, an actuation element, wherein the article can be bent by means of the bending body. This implementation is advantageous, for example for bending an article in the form of a stabilization element and, in particular, of a rod. By means of the actuation element, it is possible to act on the bending body coupled therewith and, via the latter, on the article.

By way of example, the actuation element is mounted in rotatable and/or displaceable manner on a bearing body of the bending tool. Advantageously, the bearing body is mounted in displaceable fashion on a guide of the aforementioned holding device.

It is expedient if the deformation tool comprises or forms an abutment element and, in particular, a support element for the article. The article fixed in the receptacle can rest on the abutment element and, as a result thereof, be arranged in a comparatively stable position on the deformation tool in order to make the deformation and, in particular, the bending of the article easier for the user.

It shows to be advantageous if the deformation tool comprises or forms an adjustable stop element for the article. By means of the stop element, it is possible to set, and thereby limit, the extent of the deformation, for example by way of the bending body specified above. The stop element can be formed by, or formed integrally with, the abutment element specified above. Advantageously, the stop element is held in a securable, movable manner on a bearing body of the deformation tool. By setting the position of the stop element, the user can preset the extent to which the article is deformed by means of the deformation tool.

It is expedient if a marking device of the deformation tool is held on the actuation element. By means of the navigation system, it is possible to determine the movement of the actuation element and hence of the bending body. From this, it is possible to ascertain the deformation of the article.

As an alternative or in addition thereto, provision can be made for a marking device of the deformation tool to be held on the stop element. The position of the stop element on the deformation device (for example, relative to the bearing body, the receptacle and/or the holding device overall) can be determined by the navigation system and it is possible to determine the extent of the deformation to be expected in this way.

The deformation tool can be a deformation tool that is actuatable by hand or by means of a drive. The deformation device can comprise a corresponding drive.

The present invention further relates to a medical deformation system. The object set forth at the outset is achieved by a medical deformation system, comprising a deformation device of the type set forth above and a medical navigation system for detecting and tracking the marking devices of the deformation device, wherein the relative position of the receptacle and of the deformation tool is determinable by the navigation system for the purposes of determining a deformation position of the article, and wherein the extent of the deformation of the article at the deformation position is determinable with the navigation system.

On the basis of the marking devices as explained above, the navigation system is able to determine the deformation position adopted by the deformation tool, in particular whether it is arranged at a desired deformation position. Moreover, it is possible to check the extent of the deformation, to see whether the latter corresponds to a desired deformation. As explained above, a marking device can be held particularly on the actuation element and/or on the stop element as explained above.

It is expedient if a desired shape of the article is stored in a memory unit and if the navigation system comprises or forms a notification device. In particular, at least one notification in respect of the deformation tool assuming a desired deformation position relative to the receptacle, particularly when moving the deformation tool relative to the receptacle, can be output at the notification device. Without a priori knowledge, the user can be informed, for example when moving and, in particular, displacing the deformation tool, that the latter assumes the correct position. A notification can be output to the user, for example optically, acoustically and/or haptically. As an alternative or in addition thereto, it is possible to provide the notification that the deformation of the article that is produced or producible by means of the deformation tool coincides with a desired deformation. By way of example, the movement of the actuation element is determined by the navigation system and the deformation arising as a result thereof is determined. As an alternative or in addition thereto, the position and/or the movement of the stop element can be established and the deformation to be expected can be determined. In both cases, the user can be informed by way of an appropriate notification that the desired deformation is obtained or will be obtained.

The article can be deformed at multiple positions or multiple times. To this end, it is expedient if the desired shape is subdividable into individual segments by the navigation system, wherein notifications are providable in sequence at the notification device that a respective segment corresponds to a desired shape of the respective segment as a result of deforming the article at a desired deformation position with a desired deformation. The article can be deformed segment-by-segment. The correct deformation of each segment can be monitored, verified and confirmed in sequence by the navigation system.

By way of example, relative to the receptacle, the segments are deformed successively from distal to proximal.

In an advantageous embodiment, provision can be made for deformation information items to be transmittable from the navigation system to at least one drive of the deformation device for the purposes of a machine deformation of the article in accordance with the deformation information items. It is conceivable for a deformation of the article to be able to be carried out by machine, without input by the user.

The present invention further relates to a method for deforming a medical article. A method according to the invention, achieving the object set forth at the outset, for deforming a medical article provides the use of a deformation system of the type set forth above, wherein the navigation system is used to determine a deformation position of the medical article to be deformed and an extent of the deformation of the article at the deformation position is determined.

The advantages of the method according to the invention were already mentioned in conjunction with the explanations of the deformation device and the deformation system. Reference is made to the explanations provided above. Advantageous exemplary embodiments of the method arise from advantageous embodiments of the deformation device and of the deformation system.

Figure 2:
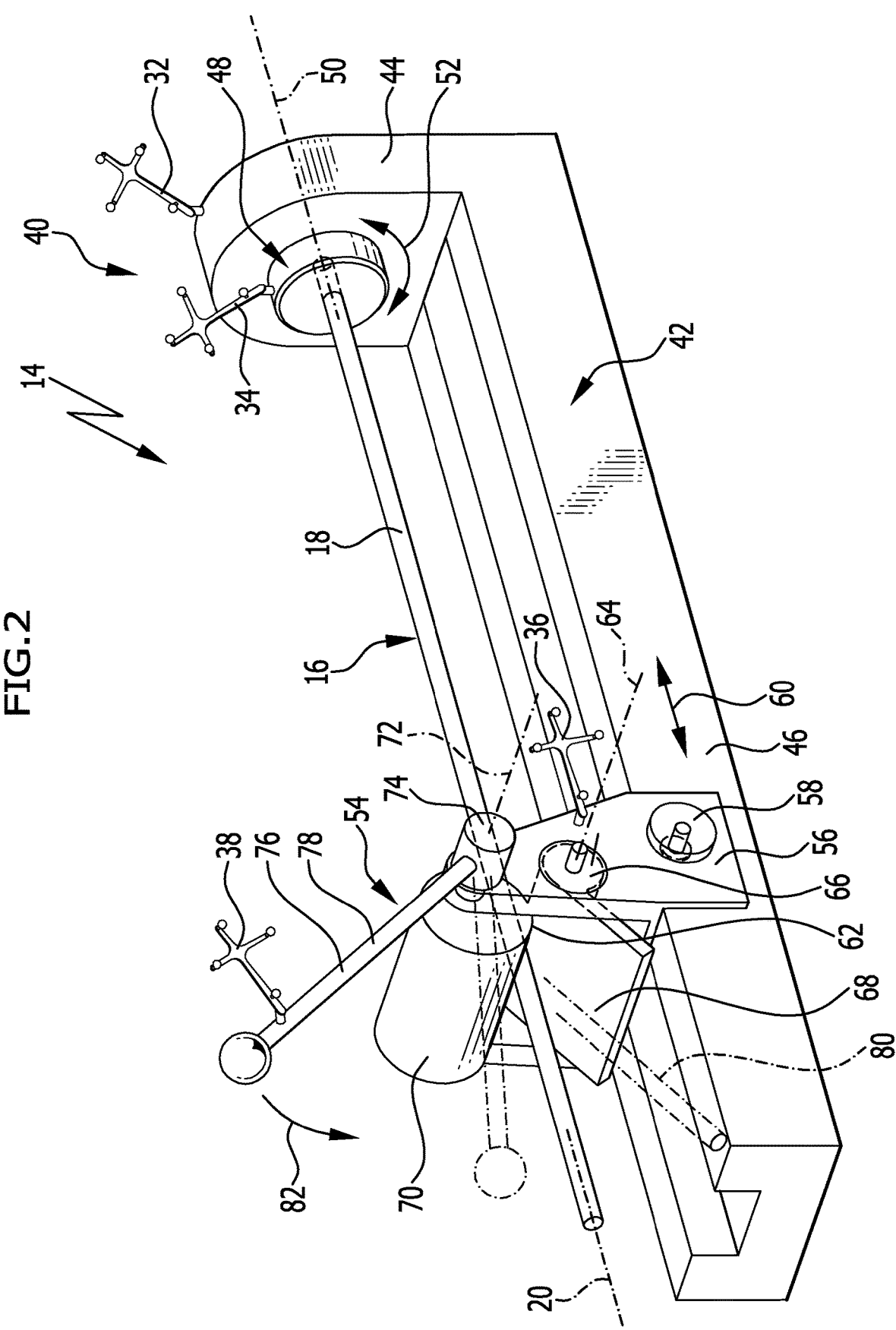
FIG. 2 shows an enlarged illustration of the deformation device in FIG. 1.

FIG. 1 shows a deformation system according to the invention, denoted overall by the reference numeral 10, in a perspective schematic illustration. The deformation system 10 has a medical navigation system 12 and a medical deformation device 14. The deformation system 10 serves to deform a medical article 16 in a defined manner. In the present case, the article 16 is configured as a stabilization element of a medical fixation system (this, in itself, is not illustrated in the drawing), in particular as a rod 18 which defines an axis 20 (FIG. 2).

The navigation system 12 is configured in a manner known per se and comprises a data processing device 22, a detection device 24 and a notification device 26. In the present case, the detection device 24 is configured as a navigation camera 28, for example as a stereo camera, and coupled to the data processing device 22. The notification device 26 is likewise coupled to the data processing device 22. The data processing device 22 comprises a memory unit 30.

By way of example, on the basis of pre-surgical or intra-surgical planning data, a desired shape of the rod 18 is stored in the memory unit 30. By way of example, the desired shape comprises information items about the extent to which the rod 18 should be deformed or is to be deformed at which deformation positions so that anchoring elements of the fixation system, not illustrated in the drawing, can be connected to the rod 18.

To this end, the desired shape of the rod 18 can be subdivided into different segments. Which desired deformation should be carried out at what desired deformation position by means of the deformation device 14 can be stored relative to a respective segment in order to ensure the desired deformation of the rod 18.

Using the navigation system 12, medical marking devices can be detected and tracked (tracking) in respect of position and/or orientation relative to the navigation system 12 in a manner known per se.

In the present case, four marking devices 32, 34, 36 and 38 comprised by the deformation device 14 are provided.

In the present case, the marking devices 32 to 38 have such a different configuration from one another that they can be unambiguously identified and distinguished from one another by the navigation system 12. The navigation system 12 has information about the component of the deformation device 14 at which a respective marking device 32 to 38 is fixed; this will be discussed in more detail below.

In the present case, the marking devices 32 to 38 are configured passively as so-called "rigid bodies", which reflect light emitted by the navigation camera 28. As an alternative or in addition thereto, the use of active marking devices is conceivable.

As is clear from FIG. 2, in particular, the deformation device 14 is a bending device 40 for bending the rod 18. The bending device 40 comprises a holding device 42 configured in pedestal-type manner, for example having a holding projection 44 at one end side. The holding projection 44 projects from a guide 46, e.g., configured as a rail.

The marking device 32 is fixed on at the holding projection 44. In this way, it is possible to determine the position and/or orientation of the bending device 40 overall relative to the navigation system 12. This offers the advantage of the bending device 40 not needing to be fixed in stationary manner during use but instead being able to be moved relative to the navigation system 12.

A receptacle 48 for the rod 18 is fixed on the holding projection 44. The receptacle 48 defines an axis 50 that is aligned with the axis 20 of the rod 18 inserted into the receptacle 48.

For the purposes of fixing the rod 18, the receptacle 48 can be configured to be similar to a drill chuck. The rod 18 can be held in the receptacle 48 in force-locking and/or positive-locking manner.

The receptacle 48 is configured to be rotatable relative to the holding projection 44 and, in particular, mounted on the latter in a manner rotatable about the axis 50 (double-headed arrow 52).

The marking device 34 is held on the receptacle 48. A rotation of the rod 18 about the axis 50 and hence about the axis 20 of the rod 18 can be determined by the navigation system 12 in this way.

Further, the bending device 40 comprises a deformation tool 54 which, in the present case, is configured in particular as a bending tool for bending the rod 18.

The deformation tool 54 comprises a bearing body 56. The bearing body 56 is displaceably mounted on the guide 46 and can be displaced along the axis 20. By way of example, the bearing body 56 can be fixed immovably to the guide 46 by means of a securing element 58. The double-headed arrow 60 denotes the displacement direction of the bearing body 56.

The bearing body 56 is configured as a bearing block. An abutment element 62 of the deformation tool 54 is held on the bearing body 56. In particular, the abutment element 62 forms a support element for the rod 18. Preferably, the abutment element 62 is arranged in such a way that the rod 18 supported thereon is aligned parallel to the displacement direction of the bearing body 56 when it is fixed in the receptacle 48.

The abutment element 62 is held in a securable, movable manner on the bearing body 56 and, in particular, mounted in pivotable manner about a pivot axis 64. For the purposes of securing the abutment element 62, provision is made of a securing element 66. The pivot axis 64 is oriented transversely to the axis 50 and to the guide 46.

The deformation tool 54 comprises a stop element 68 for delimiting the deformation of the rod 18. In the present case, the stop element 68 has a plate-shaped configuration and it is preferably formed in integral manner with the abutment element 62 such that these, together, have a substantially P-shaped cross section. By pivoting the abutment element 62 about the pivot axis 64, it is likewise possible to pivot the stop element 68 such that the free end thereof is arranged closer or less close to the guide 46. In this way, the angle between the abutment element 62 and the guide 46, and hence also the angle relative to the axis 50 are altered.

It is understood that the option of pivoting the stop element 68 relative to the bearing body 56 is advantageous. As a result of the integral configuration of the abutment element 62 and the stop element 68 in the present case, the abutment element 62 is also pivoted in the process. Should the elements be separate components, provision can be made of an immovable fixation of the abutment element 62 and provision can be made of a pivotable mounting of the stop element 68 at the bearing body 56.

Further, the deformation tool 54 comprises a bending body 70. The bending body 70 is arranged at a spacing from the abutment element 62 such that an interspace for guiding through the rod 18 is present therebetween. The bending body 70 is mounted in pivotable manner about a pivot axis 72 on the bearing body 56. The pivot axis 72 is oriented transversely to the axis 50 and to the guide 46, and also parallel to the pivot axis 64.

The bending body 70 is arranged eccentrically relative to the pivot axis 72 and, for example, it has a substantially cylindrical form. The pivot axis 72 is defined by a shaft 74, to which an actuation element 76 of the deformation tool 54 is fixed. In the present case, the actuation element 76 forms a lever 78.

By pivoting the actuation element 76 about the pivot axis 72, the bending body 70 is pivoted in eccentric manner relative to the pivot axis 72. Here, a bending force can be applied to the rod 18. The rod 18 can be bent until it abuts on the stop element 68. This is symbolized by the dash—dotted contour 80 in FIGS. 2 and 3.

The marking device 36 is fixed to the bearing body 56. This allows the navigation system 12 to determine the defined relative position in which the bearing body 56 and hence the deformation tool 54 and the receptacle 48 are arranged. When displacing the bearing body 56, this change of the relative position can be determined. Since the rod 18 is held in the receptacle 48, the navigation system 12 also can determine the position of the deformation tool 54 relative to the rod 18.

In the deformation device 14, the marking device 38 is fixed to the actuation element 76. When the actuation element 76 is pivoted, the movement can be determined by the navigation system 12. From this, it is possible to determine the extent to which the bending body 70 is moved. In this way, the navigation system 12 can calculate the extent to which the rod 18 is deformed and, in particular, bent.

Below, the functionality of the deformation system 10 and of the deformation device 14, and the course of the method are explained.

The rod 18, which originally had a straight-lined extent, for example, should be brought into the desired shape stored in the memory unit 30. To this end, as mentioned previously, the desired shape can be subdivided into a plurality of segments and the rod 18 can be successively bent. Here, the rod 18 is preferably bent from distal to proximal relative to the receptacle 48.

The navigation system 12 checks whether the bearing body 56, and hence the deformation tool 54, is positioned in the correct desired deformation position relative to the receptacle 48, for example by using the marking devices 34 and 36. At the notification device 26, a notification to displace the bearing body 56 can be provided for the user. If the bearing body 56 adopts the desired deformation position, a corresponding notification can be provided at the notification device 56.

In the present case, the screen of the navigation system 12 is used as notification device 26. In addition to an optical output of a notification, an acoustic output of a notification is conceivable.

Subsequently, the rod 18 is bent at the desired deformation position by virtue of the actuation element 76 having a bending force applied thereto (arrow 82). The movement of the actuation element 76 is tracked by the navigation system 12. If the desired bending angle, as determined on the basis of the movement of the actuation element 76, is reached, a corresponding notification can be provided at the notification device 26. In this way, the navigation system 12 can determine that the first segment has adopted the correct desired form.

During the further course of the method, the bearing body 56 can be displaced further along the guide 46 up to a subsequent desired deformation position. After it has been reached, accompanied by an appropriate notification to the user, it is possible to once again carry out bending. A notification is provided when the correct bending angle is reached. In this way, the desired shape of the second segment is checked.

Now, the rod 18 can be successively converted into the desired shape sought for by displacing the bearing body 56 and bending the rod 18. Advantageously, the securing element 58 ensures that the desired deformation position of the bearing body 56 is maintained prior to each bending.

In the example specified above, the rod 18 is bent in a plane. If bending is to be carried out in mutually different planes, the bending plane can be modified prior to the respective instance of bending by rotating the rod 18 about the axis 20. The rotation can be determined by the navigation system 12 on the basis of the marking device 34. Once the correct bending plane has been reached, a corresponding notification can be output at the notification device 26 in this case too.

By way of the manner specified above, there is the option in the deformation device 14 according to the invention of monitoring by means of the navigation system 12 each degree of freedom, namely a rotation of the rod 18 about the axis 50, a bending position by the displacement of the deformation tool 54 and a bending angle by means of the pivoting of the actuation element 76. Additionally, the position of the deformation device 14 in space can be determined relative to the navigation system 12.

Figure 3:
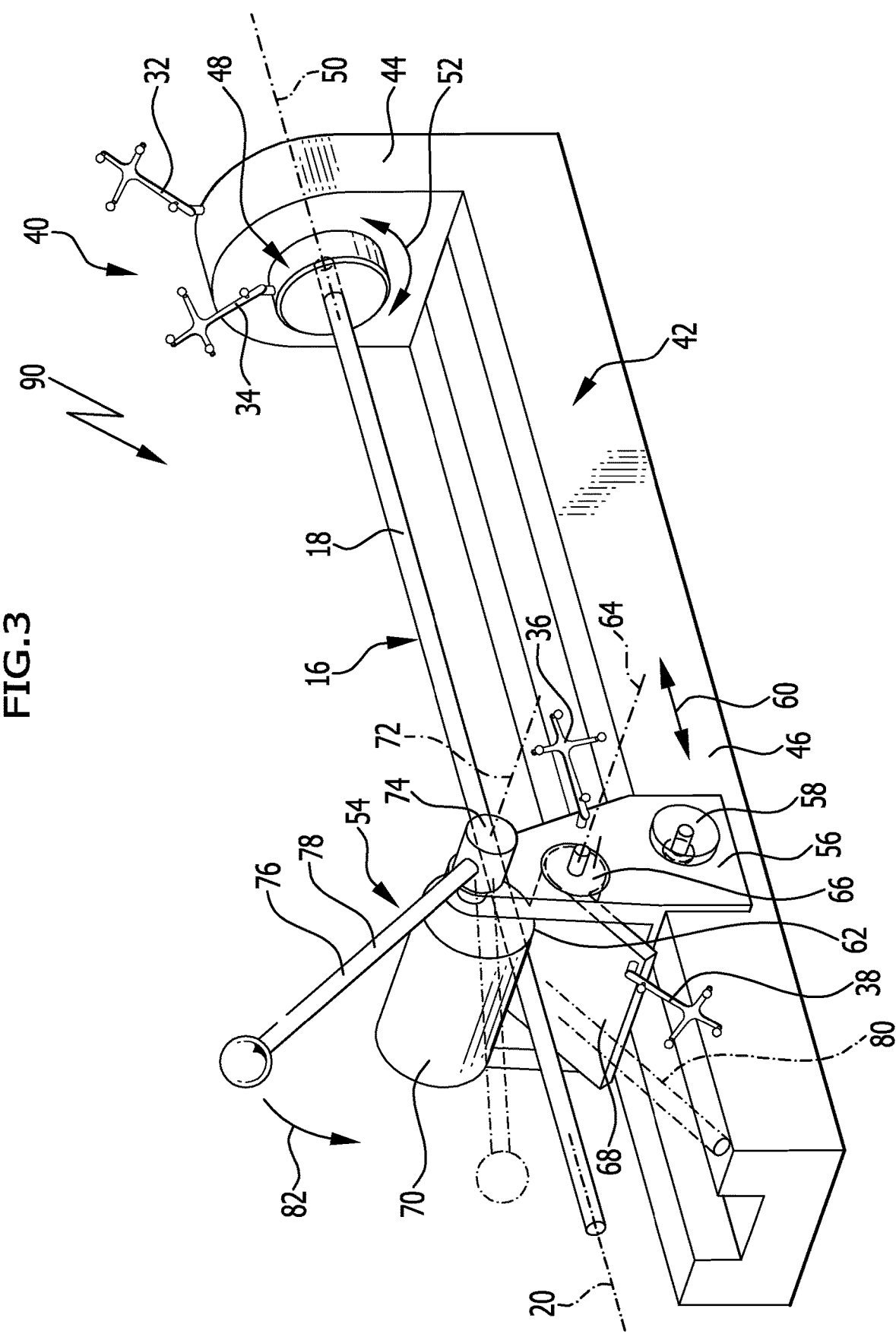
FIG. 3 shows a further preferred embodiment of the deformation device according to the invention, which can be a constituent part of the deformation system according to the invention, for example in place of, or in addition to, the deformation device in FIG. 1.

In a manner corresponding to FIG. 2, FIG. 3 shows, denoted by the reference numeral 90, an advantageous embodiment of a deformation device according to the invention that could be a constituent part of a navigation system according to the invention instead of, or together with, the deformation device 14.

Identical reference numerals are used for equivalent features and components or features and components with an equivalent effect. The advantages that are obtainable by the deformation device 14 can likewise be obtained by the deformation device 90, and so reference can be made to the explanations made above. Only the substantial differences are explained.

The marking device on the actuation element 76 is dispensed with in the deformation device 90. Instead, the marking device 38 is held on the stop element 68. In this way, the navigation system 12 is able to determine the extent to which the rod 18 can be bent at most, under the assumption that the rod 18 is in fact bent up to the stop on the stop element 68.

Prior to the bending, the user can pivot the stop element 68 about the pivot axis 64, preferably on the basis of a notification of the navigation system 12. If the stop element 68 assumes the correct desired position for the bending to be carried out, a notification to this effect can be provided. The user can fix the stop element 68 by means of the securing element 66. Subsequently, the rod 18 can be bent. Upon abutment on the stop element 68, the user knows that the desired bending angle has been reached.

Naturally, provision can be made for a respective marking device to be held both on the actuation element 76 and on the stop element 68.

LIST OF REFERENCE NUMERALS

10 Deformation system
12 Navigation system
14 Deformation device
16 Article
18 Rod
20 Axis
22 Data processing device
24 Detector device
26 Notification device
28 Navigation camera
30 Memory unit
32 Marking device
34 Marking device
36 Marking device
38 Marking device
40 Bending device
42 Holding device
44 Holding projection
46 Guide
48 Receptacle
50 Axis
52 Double-headed arrow
54 Deformation tool
56 Bearing body
58 Securing element
60 Double-headed arrow
62 Abutment element
64 Pivot axis
66 element
68 Stop element
70 Bending body
72 Pivot axis
74 Shaft
76 Actuation element
78 Lever
80 Contour
82 Arrow
90 Deformation device

What is claimed is:

1. Medical deformation device for a medical article, comprising:
 a receptacle for fixing the article,
 a deformation tool used to act on the article for deformation purposes, the deformation tool being movable in a defined manner relative to the receptacle, and
 a respective first medical marking device that is detectable by a navigation system being held on the receptacle and a respective second marking device that is detectable by the navigation system being held on the deformation tool for the purposes of determining a relative position of the deformation tool and the receptacle,
 wherein:
 the deformation device comprises a holding device,
 the receptacle is rotatably mounted on the holding device, the deformation tool is held in movable manner on the holding device, and a third marking device is fixed to the deformation tool for the purposes of determining, by means of the navigation system, an extent of a deformation of the article.

2. Deformation device in accordance with claim 1, wherein the deformation tool is configured to be displaceable relative to the receptacle.

3. Deformation device in accordance with claim 1, wherein the holding device comprises or forms a guide for a bearing body of the deformation tool, wherein the second marking device is held on the bearing body.

4. Deformation device in accordance with claim 1, wherein the deformation device comprises a medical marking device held on the holding device for the purposes of determining at least one of the position and orientation of the deformation device relative to the navigation system.

5. Deformation device in accordance with claim 1, wherein the receptacle defines an axis that is aligned with an axis defined by the article, said article having a longitudinal extent and being fixed in the receptacle.

6. Deformation device in accordance with claim 1, wherein the receptacle is configured to be rotatable relative to the holding device, the rotation being actuated manually or by means of a drive.

7. Deformation device in accordance with claim 1, wherein there is at least one of the following:
   a movement of the deformation tool relative to the receptacle is actuated manually or by means of a drive;
   the deformation tool is actuatable by hand or by means of a drive.

8. Deformation device in accordance with claim 1, wherein the deformation tool is a bending tool and comprises a bending body and, coupled therewith, an actuation element so as to bend the article by means of the bending body.

9. Deformation device in accordance with claim 8, wherein the actuation element is mounted in at least one of a rotatable and displaceable manner on a bearing body of the bending tool.

10. Deformation device in accordance with claim 8, wherein the third marking device is held on the actuation element.

11. Deformation device in accordance with claim 1, wherein the deformation tool comprises or forms an abutment element for the article.

12. Deformation device in accordance with claim 1, wherein the deformation tool comprises or forms an adjustable stop element for the article for the purposes of restricting the deformation of the article.

13. Deformation device in accordance with claim 12, wherein a further marking device of the deformation device is held on the stop element.

14. Medical deformation system, comprising:
   a deformation device for a medical article, the deformation device comprising a receptacle for fixing the article, a deformation tool used to act on the article for deformation purposes, the deformation tool being movable in a defined manner relative to the receptacle, and a respective first medical marking device being held on the receptacle and a respective second marking device that is detectable by the navigation system being held on the deformation tool for the purposes of determining a relative position of the deformation tool and the receptacle, wherein a third marking device is fixed to the deformation tool for the purposes of determining an extent of a deformation of the article, and
   a medical navigation system for detecting and tracking the marking devices of the deformation device,
   wherein:
      the deformation device comprises a holding device,
      the receptacle is rotatably mounted on the holding device,
      the deformation tool is held in movable manner on the holding device,
      the relative position of the receptacle and of the deformation tool is determinable by the navigation system for the purposes of determining a deformation position on the article, and
      the extent of the deformation of the article at the deformation position is determinable with the navigation system.

15. Deformation system in accordance with claim 14, wherein a desired shape of the article is stored in a memory unit and wherein the navigation system comprises or forms a notification device for providing at least one notification in respect of:
   the deformation tool assuming a desired deformation position relative to the receptacle when moving the deformation tool relative to the receptacle;
   the deformation of the article that is produced or producible by means of the deformation tool coinciding with a desired deformation.

16. Deformation system in accordance with claim 15, wherein the desired shape is subdividable into individual segments by the navigation system, wherein notifications are providable in sequence at the notification device that, by deformation of the article at a desired deformation position with a desired deformation, a respective segment coincides with a desired shape of the respective segment.

17. Deformation system in accordance with claim 14, wherein deformation information items are transmittable from the navigation system to at least one drive of the deformation device for the purposes of a machine deformation of the article in accordance with the deformation information items.

18. Method for deforming a medical article using a deformation system, the deformation system comprising:
   a deformation device for a medical article, the deformation device comprising a receptacle for fixing the article, a deformation tool used to act on the article for deformation purposes, the deformation tool being movable in a defined manner relative to the receptacle, and a respective first medical marking device being held on the receptacle and a respective second marking device that is detectable by the navigation system being held on the deformation tool for the purposes of determining a relative position of the deformation tool and the receptacle, wherein a third marking device is fixed to the deformation tool for the purposes of determining an extent of a deformation of the article, wherein the deformation device comprises a holding device, the receptacle is rotatably mounted on the holding device, and the deformation tool is held in movable manner on the holding device, and
   a medical navigation system for detecting and tracking the marking devices of the deformation device,
   wherein the method comprises:
      determining, using the navigation system, a deformation position of the medical article to be deformed, and
      ascertaining, using the navigation system, an extent of the deformation of the article at the deformation position.

19. Medical deformation device for a medical article, comprising:
- a receptacle for fixing the article,
- a deformation tool used to act on the article for deformation purposes, the deformation tool being movable in a defined manner relative to the receptacle, and
- a respective first medical marking device that is detectable by a navigation system being held on the receptacle and a respective second marking device that is detectable by the navigation system being held on the deformation tool for the purposes of determining a relative position of the deformation tool and the receptacle, wherein:
- the receptacle is rotatable so as to rotate the article about an axis of rotation of the receptacle which is coaxial with a longitudinal axis of the article,
- the receptacle is rotated to enable deformation of the article to be carried out in mutually different planes of deformation, and
- a third marking device is fixed to the deformation tool for the purposes of determining, by means of the navigation system, an extent of a deformation of the article.

* * * * *